(12) United States Patent
Garcia et al.

(10) Patent No.: US 11,254,967 B2
(45) Date of Patent: Feb. 22, 2022

(54) SALIVARY UREA NITROGEN RAPID DETECTION

(71) Applicants: DIGNITY HEALTH, San Francisco, CA (US); ARIZONA BOARD OF REGENTS ON BEHALF OF ARIZONA STATE UNIVERSITY, Scottsdale, AZ (US)

(72) Inventors: Antonio Garcia, Chandler, AZ (US); Abraham Lieberman, Phoenix, AZ (US)

(73) Assignees: Dignity Health, San Francisco, CA (US); Arizona Board of Regents on Behalf of Arizona State University, Scottsdale, AZ (US)

(*) Notice: Subject to any disclaimer, the term of this patent is extended or adjusted under 35 U.S.C. 154(b) by 246 days.

(21) Appl. No.: 16/605,695

(22) PCT Filed: Apr. 17, 2018

(86) PCT No.: PCT/US2018/027916
§ 371 (c)(1),
(2) Date: Oct. 16, 2019

(87) PCT Pub. No.: WO2018/195043
PCT Pub. Date: Oct. 25, 2018

(65) Prior Publication Data
US 2020/0131559 A1    Apr. 30, 2020

Related U.S. Application Data

(60) Provisional application No. 62/486,340, filed on Apr. 17, 2017, provisional application No. 62/505,572, filed on May 12, 2017.

(51) Int. Cl.
*G01N 33/62*    (2006.01)
*G01N 33/70*    (2006.01)
(Continued)

(52) U.S. Cl.
CPC ............ *C12Q 1/58* (2013.01); *A61B 10/0051* (2013.01); *G01N 33/62* (2013.01); *G01N 33/70* (2013.01);
(Continued)

(58) Field of Classification Search
CPC .... A61B 10/0051; C12Q 1/58; G01N 33/487; G01N 33/62; G01N 33/70;
(Continued)

(56) References Cited

U.S. PATENT DOCUMENTS 3,530,040 A * 9/1970 Hendershot .............. C12Q 1/58
                                                    435/12
3,873,269 A * 3/1975 Kraffczyk ................ C12Q 1/58
                                                    435/12
(Continued)

FOREIGN PATENT DOCUMENTS

CA    1317532 C    5/1993
DE    3240463 A1   6/1983
(Continued)

OTHER PUBLICATIONS

Akai, T., et al. "Salivary urea nitrogen as an index to renal function: a test-strip method." Clinical chemistry 29.10 (1983): 1825-1827.
(Continued)

*Primary Examiner* — Maureen Wallenhorst
(74) *Attorney, Agent, or Firm* — Quarles & Brady LLP; Yakov Sidorin

(57) ABSTRACT

Apparatus and methods for measuring a concentration of a target molecule from a biological sample are disclosed. In one example, the apparatus includes a porous pad, which is impregnated with a solution containing at least one agent and which contains an unfilled capillary matrix, a housing for the porous pad, and a membrane that covers the porous pad.

27 Claims, 8 Drawing Sheets

(51) Int. Cl.
*C12Q 1/58* (2006.01)
*A61B 10/00* (2006.01)

(52) U.S. Cl.
CPC ............... *Y10T 436/147777* (2015.01); *Y10T 436/171538* (2015.01); *Y10T 436/175383* (2015.01)

(58) Field of Classification Search
CPC ........ Y10Y 436/147777; Y10Y 436/17; Y10Y 436/171538; Y10Y 436/175383; Y10Y 436/25875; Y10T 436/147777; Y10T 436/17; Y10T 436/171538; Y10T 436/175383; Y10T 436/25875
USPC ... 436/63, 98, 106, 108, 113, 164, 167, 169, 436/181; 422/400, 401, 402, 412, 416, 422/419, 420, 430, 83, 86, 87, 88; 435/12
See application file for complete search history.

(56) References Cited

U.S. PATENT DOCUMENTS

| | | | |
|---|---|---|---|
| 4,101,382 A | 7/1978 | Chang | |
| 4,176,008 A * | 11/1979 | Figueras | C12Q 1/58 422/52 |
| 4,223,089 A | 9/1980 | Rothe | |
| 4,271,264 A | 6/1981 | Modrovich | |
| 4,282,316 A | 8/1981 | Modrovich | |
| 4,548,906 A | 10/1985 | Sekikawa | |
| 5,130,231 A | 7/1992 | Kennedy | |
| 5,137,692 A * | 8/1992 | Fritz | A61B 5/00 422/401 |
| 5,804,452 A * | 9/1998 | Pronovost | C12Q 1/26 422/420 |
| 6,303,081 B1 | 10/2001 | Mink | |
| 6,365,417 B1 | 4/2002 | Fleming | |
| 7,022,285 B2 * | 4/2006 | Arai | G01N 31/223 422/423 |
| 7,344,301 B2 | 3/2008 | Garcia | |
| 8,611,992 B2 | 12/2013 | Goldstein | |
| 9,995,688 B2 | 6/2018 | Garcia | |
| 2004/0050435 A1 | 3/2004 | Hayes | |
| 2005/0032051 A1 | 2/2005 | Hayes | |
| 2008/0021429 A1 | 1/2008 | Klofta | |
| 2008/0050451 A1 | 2/2008 | Mabry | |
| 2008/0213853 A1 | 9/2008 | Garcia | |
| 2008/0274014 A1 | 11/2008 | Jumonville | |
| 2009/0011436 A1 | 1/2009 | Piasio | |
| 2009/0078326 A1 | 3/2009 | Rosario | |
| 2009/0157024 A1 | 6/2009 | Song | |
| 2010/0159599 A1 | 6/2010 | Song | |
| 2010/0159611 A1 | 6/2010 | Song | |
| 2010/0239458 A1 * | 9/2010 | Mink | B01L 3/5023 422/420 |
| 2010/0254581 A1 | 10/2010 | Neeser | |
| 2010/0330684 A1 | 12/2010 | O'Connor | |
| 2011/0076776 A1 | 3/2011 | Stewart | |
| 2012/0276568 A1 | 11/2012 | Nakamura | |
| 2015/0157300 A1 | 6/2015 | Ealovega | |

FOREIGN PATENT DOCUMENTS

| | | |
|---|---|---|
| EP | 0005519 A2 | 11/1979 |
| EP | 0524596 A1 | 1/1993 |
| JP | S5877663 A | 5/1983 |
| JP | S58193459 A | 11/1983 |
| WO | 1999006827 A2 | 2/1999 |
| WO | 2000021665 A1 | 4/2000 |
| WO | 2000021665 A9 | 4/2000 |
| WO | 2001089985 A2 | 11/2001 |
| WO | 2001098785 A2 | 12/2001 |
| WO | 2001098785 B1 | 11/2002 |
| WO | 2004000446 A2 | 12/2003 |
| WO | 2006132640 A2 | 12/2006 |
| WO | 2007101174 A2 | 9/2007 |
| WO | 2011034678 A1 | 3/2011 |
| WO | 2011104567 A1 | 9/2011 |
| WO | 2018195043 A1 | 10/2018 |
| WO | 2019014373 A1 | 1/2019 |
| WO | 2020256941 A1 | 12/2020 |

OTHER PUBLICATIONS

Clingan, H., et al. "Viscous Fingering of Miscible Liquids in Porous and Swellable Media for Rapid Diagnostic Tests." Bioengineering 5.4 (2018): 94.
DripDrop.com. 5 Gadgets that Detect Hydration. Blog post. Dec. 14, 2014. Available online at https://web.archive.org/web/20161206173953/https://dripdrop.com/5-futurist-gadgets-detect-dehydration/.
Cardoso E.M.L., et al. Assessment of salivary urea as a less invasive alternative to serum determinations. Scand. J. Clin. Lab. Investig. 2009;69:330-334.
Fu X., et al. Viscous Fingering with Partially Miscible Fluids. Phys. Rev. F. 2017;2:104001. doi: 10.1103/PhysRevFluids.2.104001.
Gekko K., et al. Mechanism of protein stabilization by glycerol: Preferential hydration in glycerol-water mixtures. Biochemistry. 1981;20:4667-4676. doi: 10.1021/bi00519a023.
Homsy G.M. Viscous fingering in porous media. Annu. Rev. Fluid Mech. 1987;19:271-311. doi: 10.1146/annurev.fl.19.010187.001415.
Huan, X, et al. Epidermal impedance sensing sheets for precision hydration assessment and spatial mapping. IEEE Trans. Biomed. Eng. 2013, 60, 2848-2857.
International Searching Authority. International Search Report and Written Opinion for application PCT/US2018/027916. dated Jul. 6, 2018. 10 pages.
International Searching Authority. International Search Report and Written Opinion for application PCT/US2020/036000. dated Aug. 20, 2020. 8 pages.
Knox K.T., et al. Recovery of handwritten text from the diaries and papers of David Livingstone; Proceedings of the Computer Vision and Image Analysis of Art II Conference, IS&T/SPIE Electronic Imaging Symposium; San Francisco, CA, USA. Jan. 23-27, 2011.
Kostin I., et al. Modeling of Miscible Liquids with the Korteweg Stress. ESAIM-Math. Model. Numer. Anal. 2003;37:741-753. doi: 10.1051/m2an:2003042.
Masoodi R., et al. Darcy's law-based model for wicking in paper-like swelling porous media. AIChE J. 2001;56:2257-2267. doi: 10.1002/aic.12163.
Ogawa, J., et al. "A new enzymatic method for the measurement of creatinine involving a novel ATP-dependent enzyme, N-methylhydantoin amidohydrolase." Bioscience, biotechnology, and biochemistry 59.12 (1995): 2292-2294.
Saffman P.G., et al. The Penetration of a Fluid into a Porous Medium or Hele-Shaw Cell Containing a More Viscous Liquid. Proc. R. Soc. Lond. A. 1958;245:312-328. doi: 10.1098/rspa.1958.0085.
Pramanik, S., et al. Linear stability analysis of Korteweg stresses effect on miscible viscous fingering in porous media. Phys. Fluids. 2013;25:074104.
Schmidt, F. et al. Ammonia in breath and emitted from skin. J. Breath Res. 2013, 7, 1-30.
Stevar M.S.P., et al. Shapes and dynamics of miscible liquid/liquid interfaces in horizontal capillary tubes. J. Colloid Interface Sci. 2012;383:184-197. doi: 10.1016/j.jcis.2012.06.053.
Suekane T., et al. Three-dimensional viscous fingering of miscible fluids in porous media. Phys. Rev. F. 2017;2:103902. doi: 10.1103/PhysRevFluids.2.103902.
Vanaparthy S.H., et al. Variable density and viscosity, miscible displacements in capillary tubes. Eur. J. Mech. B/Fluids. 2008;27:268-289 doi: 10.1016/j.euromechflu.2007.06.003.
European Patent Office. Extended European Search Report for application 18787508-3. dated Nov. 27, 2020. 9 pages.
Evans, R. et al., "Diagnostic Performance of a Saliva Urea Nitrogen Dipstick to Detect Kidney Disease in Malawi", Kidney International Reports, Mar. 2017 (available online Dec. 2016), vol. 2, No. 2, pp. 219-227. DOI:10.1016/i.ekir.2016.12.006.

(56) References Cited

OTHER PUBLICATIONS

U.S. Appl. No. 09/807,663, filed Jul. 2, 2001, Garcia et al.
U.S. Appl. No. 16/629,913, filed Jan. 9, 2020, Garcia et al.

* cited by examiner

SALIVARY UREA NITROGEN RAPID DETECTION

CROSS-REFERENCE TO RELATED APPLICATIONS

This application is a U.S. National Stage of PCT Application No. PCT/US2018/027916 filed on Apr. 17, 2018 which claims the benefit of U.S. Provisional Patent Application No. 62/486,340, filed on Apr. 17, 2017, and U.S. Provisional Patent Application No. 62/505,572, filed May 12, 2017, the entire contents of which are incorporated herein by reference.

STATEMENT REGARDING FEDERALLY SPONSORED RESEARCH OR DEVELOPMENT

None.

BACKGROUND

It is important and medically relevant to be able to identify patients whose blood pressure may drop to levels requiring hospitalization before they exhibit orthostatic hypotension that could lead to potentially unsafe situations or urgent medical attention/hospitalization. If properly identified with sufficient time and resources for them to regain blood volume through properly formulated liquid imbibition, the desired patient outcome, by being attentive to maintaining normal hydration, would be the minimization of hospitalizations for these groups of patients and hence an improved quality of life. Measuring hydration state could also be used in outdoor or sports activities to monitor changes in urea concentration in saliva before serious conditions occur. Another application could be in care facilities to check for proper health maintenance procedures.

There is growing interest in many bio/medical technologies involving non- or low-invasive monitoring. A dehydrated state is an interesting and complex physiological condition that has been addressed in the research literature by saliva and sweat testing and in cosmetics by skin impedance monitoring devices. Saliva and sweat testing device electronics are still in R&D stages, and there is still no accurate, rapid, and inexpensive means of determining key indicators such as urea in saliva. Moreover, wearable or non-invasive hydration meters based on skin impedance or other means have several challenges, primarily stemming from interpreting a local measurement as being a true indicator of a systemic condition such as dehydration. A confounding issue is likely due to the body's control mechanisms to maintain homeostasis leading to a series of physiologically measurable changes such as skin dryness that may or may not be directly relevant as a measure if someone becomes dehydrated.

SUMMARY

Embodiments of the current technology relate to apparatuses and methods for measuring a concentration of a target molecule from a biological sample.

In some embodiments, the apparatus comprises a porous pad, a housing for disposing the porous pad, and a membrane that covers the porous pad. Further, the porous pad is impregnated with a solution containing at least one agent and comprises an unfilled capillary matrix. The membrane is hydrophobic and gas permeable. In other embodiments, the apparatus may comprise a target molecule level indicating strip. In yet other embodiments, the apparatus may comprise a gas sensor. In yet other embodiments, the apparatus may comprise a second porous pad impregnated with a solution containing a second agent.

Further, embodiments of the current technology disclose a salivary urea nitrogen level testing kit. The kit comprises a saliva collecting device, a porous pad, an ammonia level indicating strip, and a hydrophobic and gas permeable membrane disposed between the porous pad and the ammonia level indicating strip.

Moreover, embodiments of the current technology disclose a salivary urea nitrogen level testing kit, which comprises a saliva collecting device, a porous pad, a gas sensor, and a hydrophobic and gas permeable membrane disposed between the porous pad and the gas sensor.

These and other aspects are further described in the drawings and written description that follow.

BRIEF DESCRIPTION OF DRAWINGS

It is desirable to create a low cost and rapid test that is adequate to make a decision as to whether someone is dehydrated or at normal hydration. The technology disclosed herein will be better understood from a reading of the following detailed description taken in conjunction with the drawings in which like reference designators are used to designate like elements, and in which.

DETAILED DESCRIPTION

Embodiments of the technology discloses a rapid and low cost test and apparatuses in determining the concentration of clinically relevant molecules, such as urea, in biological fluids. For example, the concentration of urea in saliva correlates with the hydration state of a person. The test is easily administered and does not require instrumentation or expert operation.

The technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

Figure 1:
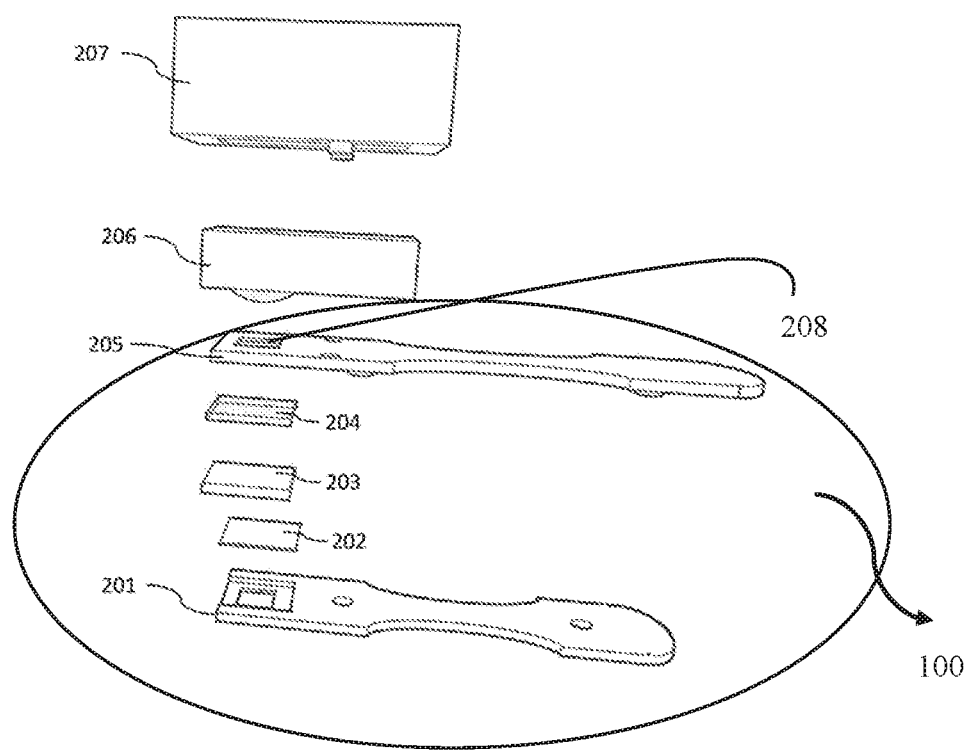
FIG. 1 is an exploded view illustrating one embodiment of test apparatus 100.
Figure 2:
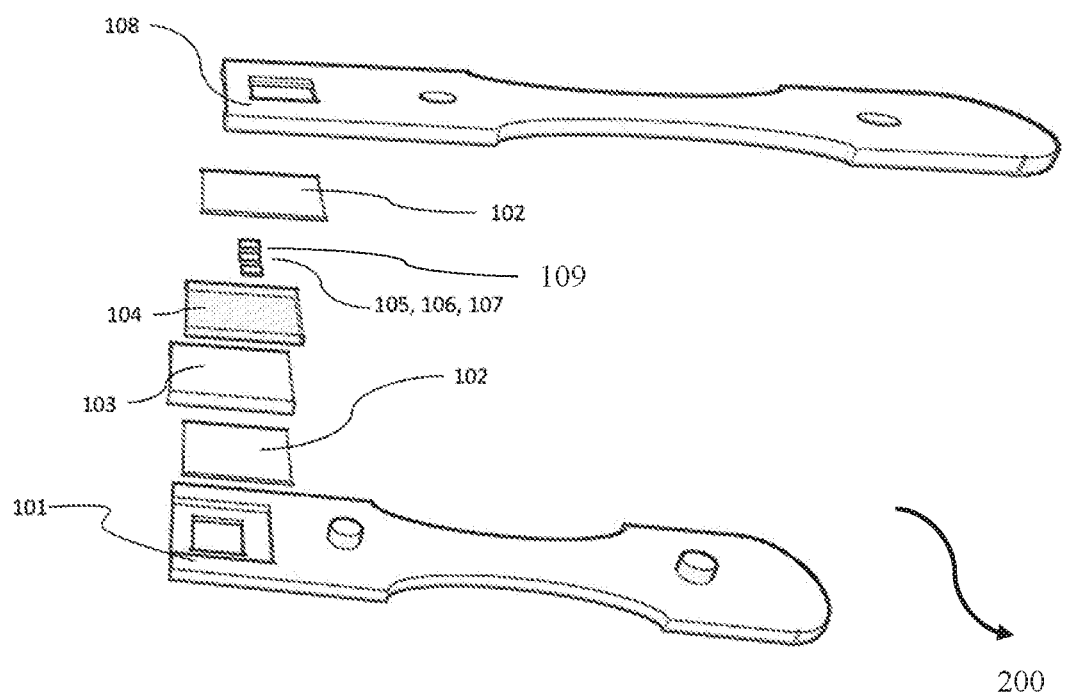
FIG. 2 is an exploded view illustrating another embodiment of test apparatus 200.
Figure 4:
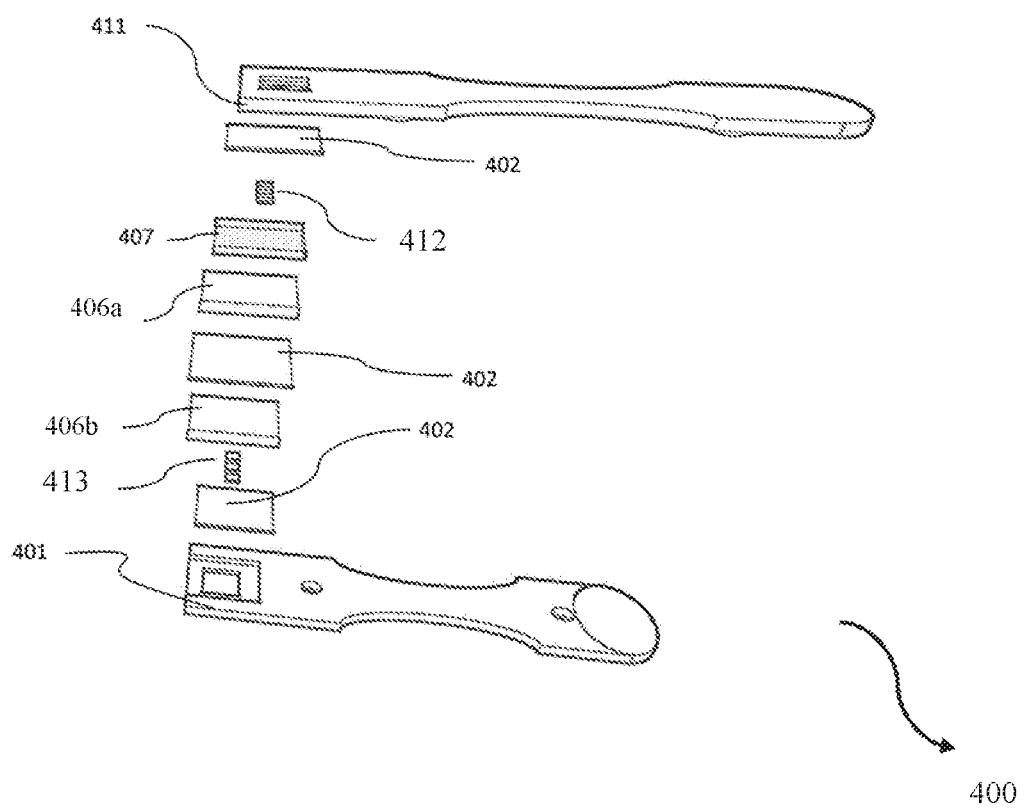
FIG. 4 is an exploded view illustrating another embodiment of test apparatus 400.

FIGS. 1, 2, and 4 illustrate different embodiments of an apparatus for measuring a concentration of a target molecule in a biological sample. Referring to FIG. 1, an embodiment of the apparatus 100 is shown. The apparatus 100 comprises among others, a bottom half housing 201, a top half housing 205, and a porous pad 203. The bottom half housing 201 and the top half housing 205 can be attached together to form a cavity for disposing the porous pad 203. In this embodiment, a membrane 204 is disposed on top of the porous pad 203 and couples to the top half housing 205. In some embodiments, the membrane 204 is made of Teflon®. In other embodiments, the membrane 204 is made of polypropylene. In yet other embodiments, the membrane 204 is made of polyethylene. Any other suitable materials that are hydrophobic and gas permeable can be used to make membrane 204. Further, a second water proof membrane 202 is disposed underneath the porous pad 203 and couples to the bottom half housing 201. Moreover, the top half housing 205 includes an opening 208 which allows a gas sensor to be in contact with the membrane 204.

FIG. 2 illustrates another embodiment of the apparatus 200 with a target molecule level indicating strip 109. Similarly, to apparatus 100, apparatus 200 comprises a bottom half housing 101, a top half housing 108, and a porous pad 103. The bottom half housing 101 and the top half housing 108 also can be attached together to form a cavity for disposing the porous pad 103. In this embodiment, a membrane 104, same as membrane 204, is disposed over the porous pad 103 and the target molecule level indicating strip 109 is disposed on top of the membrane 104. Another waterproof and transparent membrane 102 is placed over the target molecule level indicating strip 109 and couples with the top half housing 108. The top half housing 108 comprises an opening to allow observation of the target molecule level indicating strip 109 through the membrane 102.

Further, FIG. 4 illustrates another embodiment of the apparatus 400 with a second porous pad 406b. In this embodiment, the apparatus 400 comprises a bottom half housing 401, a top half housing 411, a first porous pad 406a, a second porous pad 406b. The two porous pads 406a and 406b are separated by a waterproof membrane 402 when they are disposed in a cavity formed by attaching the top half housing 411 and the bottom half housing 401.

In some embodiments, the apparatus comprises a first target molecule indicating strip 412 and a second target molecule indicating strip 413. The first target molecule is different from the second target molecule. The first target molecule indicating strip 412 is disposed on top of the first porous pad 406a with a waterproof membrane 407, same as membrane 204, placed in between. Similarly, the second target molecule indicating strip 413 is disposed underneath the second porous pad 406b. Another biomarker can be detected without the need for a membrane like membrane 407. For example, to detect hydrogen peroxide, as a reaction product, colorimetric paper that is specific for hydrogen peroxide detection can be used without a membrane.

There are also waterproof membranes 402 laying over the first target molecule indicating strip 412 and the second target molecule indicating strip 413 respectively. All plastic components in the apparatus 100/200/400 would be oral grade and sterile.

For example, apparatus 400 can be used to detect two different target molecules at the same time. In certain embodiments, the first porous pad 406a is impregnated with a first solution containing urease and the second porous pad 406b is impregnated with a second solution containing a different enzyme, which can react with creatinine to generate hydrogen peroxide. Hydrogen peroxide can be measured to determine the level of creatinine. The combined detection of urea and creatinine levels can be used to detect dehydration and assess kidney function.

Figure 3:
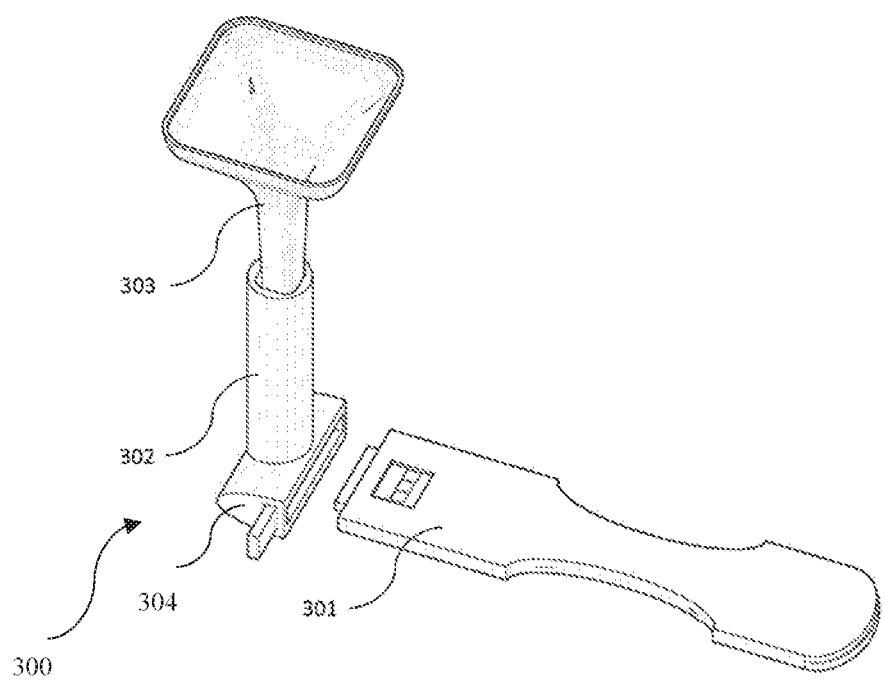
FIG. 3 shows an embodiment of a saliva collection apparatus 300 in connection with a test apparatus.

FIG. 3 illustrates an assembled apparatus 100/200/400 and an embodiment of a biological sample collecting device 300. The device 300 comprises a funnel 303, a container 302, and a tray 304. As illustrated in FIG. 3, the assembled porous pads and membranes protrude out the assembled top and bottom housing. Further, the protruded portion can be inserted into the tray 304. After collecting a biological sample, the sample flows down from the funnel 303, through the container 302, and the tray 304. When the protruded portion of the assembled apparatus 301 is inserted inside tray 304, the collected sample is able to be absorbed into the porous pad.

In order to quickly absorb and distribute a biological fluid evenly through the porous pad, the porous pads 103, 203, 406a, and 406b are impregnated with a water-miscible solution. In certain embodiments, the water-miscible solution comprises polyhydroxy organic compounds and an agent that is designed to release a target molecule from the biological fluid. In some embodiments, the agent is enzyme urease, which can cause ammonia to release from urea nitrogen contained in a biological fluid, such as saliva. Two other examples are: (1) the measurement of high levels of creatinine in saliva using the enzyme creatinine deaminase, which produces ammonia; and (2) total cholesterol could be detected using cholesterase enzyme with detection of hydrogen peroxide.

The polyhydroxy organic compounds are selected from the group consisting of glycerol, sucrose, polysorbate, ethylene glycol, propylene glycol, and a combination thereof. In certain embodiments, the water-miscible solution comprises a liquid that has a heavier density and a higher viscosity than those of the biological fluids. In a preferred embodiment, the solution contains 50% by volume of glycerol and 50% by volume of water. This solution may also comprises components that are able to increase shelf life of urease. Typically, the biological fluids can be blood, serum, plasma, urine, saliva, spinal fluid, sweat, tears, vaginal fluid, mucous, or semen.

In addition, the porous pads could be gauze or other suitable materials that have capacity to contain an unfilled capillary matrix after impregnating with the water-miscible solution. The unfilled capillary matrix allows the porous pad to be filled quickly of a biological fluid by capillary action. When the biological fluid contacts the water-miscible solution in a confined space such as a capillary inside the porous pad, Korteweg stresses occur within the porous pad due to the differences in density of the biological fluid and the water-miscible solution. Also, viscous fingering occurs when a less viscous liquid, such as the biological fluid, is introduced into a pore or capillary that contains a more viscous liquid, such as the water-miscible solution. Both phenomena occur spontaneously and have been observed to increase the contact area between the two miscible liquids and speed their combination into one liquid with a uniform density and viscosity at time-scales much faster than the time needed for Fick's law diffusion to create the same level of mixing in a liquid. When the porous pad contacts a biological fluid, the biological fluid, through capillary pressure, initially pushes the water-miscible solution further into the porous pad while also filling smaller pores that were not filled by the water-miscible solution. This process can occur within 30 seconds. Then Korteweg stresses and viscous fingering can occur over an additional period of about 10 minutes. Since the capillary filling is self-limiting, due to reaching the capacity of the porous test pad, precise operator control of sample contact time is not needed.

Further, an amount of the biological fluid absorbed by the porous pad can be adjusted over a wide range by employing porous pads with different sizes. In some embodiments, a porous pad that is about 2 mm in thickness and about 15 mm in length and width can absorb about 300 microliters of saliva quickly. Sometimes, a larger amount of biological fluid is needed in order to accumulate a target molecule for accurate measuring. To scale up or down the amount of absorbed biological samples, the width and length of the porous pads can be increased or decreased while maintaining the thickness of the porous pad at 2 mm. While particular measurements of the porous pad are described herein, these measurements are not meant to be limiting.

In embodiments of the current technology, a salivary urea nitrogen level testing kit is also contemplated. The kit further comprises a saliva collecting device, a porous pad, an ammonia level indicating strip, and a hydrophobic and gas permeable membrane disposed between the porous pad and the ammonia level indicating strip. Further, in some embodiments, the ammonia level indicating strip comprises three different levels indicated by three different colors 105, 106, 107 in FIG. 2 to show low, medium, and high levels of salivary urea nitrogen concentrations. For example, the color green indicates a normal level of salivary urea nitrogen (SUN); the color yellow indicates a borderline high level of SUN; and the color red indicates a high level of SUN, which means a subject is dehydrated. In other embodiments, the ammonia level indicating strip further comprises a liquid crystal display (LCD) readout panel, wherein the LCD readout panel is configured to display a numeric ammonia concentration.

Furthermore, another embodiment of the salivary urea nitrogen level testing kit contains a saliva collecting device, a porous pad, a gas sensor, and a hydrophobic and gas permeable membrane disposed between the porous pad and the gas sensor. In some embodiments, the ammonia gas sensor is an ammonia gas sensor Arduino MQ137 and is configured to detect and measure urea concentrations in ammonia gas. In certain embodiments, this kit may further comprise an ammonia level indicating element, which includes a LCD readout panel. The LCD readout panel may be configured to provide a numeric urea concentration after the ammonia gas sensor measures the urea concentration. Alternatively, the LCD readout panel may be configured to provide a continuous display of the increased urea concentration until reaching a maximum readout of the corresponding urea concentration by the ammonia gas sensor. When the maximum readout of the urea concentration is reached, the ammonia level indicating element may prompt a tester by sounding a beep. The maximum readout of the urea concentration may be reached after 1 minute, 3 minutes, 5 minutes, 10 minutes, or 15 minutes.

Figure 6:
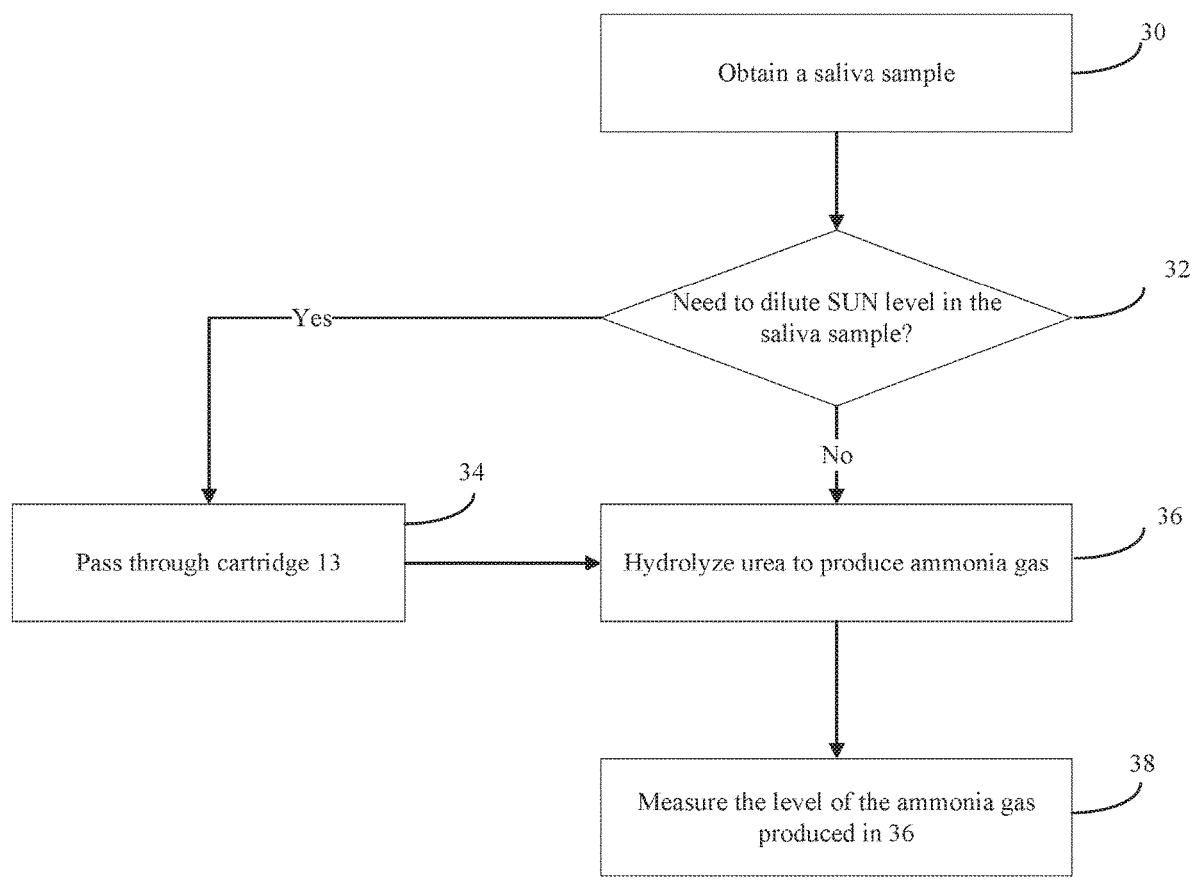
FIG. 6 illustrates an embodiment of a method of measuring hydration levels.

Now, referring to FIG. 6, a method of utilizing either of the above described kits to measure the salivary urea nitrogen (SUN) level in a saliva sample is illustrated. In step 30, a saliva sample is obtained. If the ammonia level in the saliva sample needs to be diluted, step 30 transitions to step 32 to dilute the ammonia level. In some embodiments, diluting ammonia would be useful when a high level of urea accuracy is needed under rapid dehydration due to exertion. In other embodiments, ammonia dilution in a saliva sample is not performed under gradual dehydration over a longer period of time due to environment or other conditions. If the ammonia level in the saliva sample does not need to be diluted, step 30 transitions to step 36, where the salivary urea is hydrolyzed to produce ammonia in the vapor phase. In step 38, the amount of ammonia in the vapor phase is measured either quantitatively or semi-quantitatively. In some embodiments, the ammonia gas reaches the indicator chemicals contained in ammonia level indicating strip and causes the color change of the ammonia level indicating strip. Different colors of the ammonia level indicating strip indicate different levels of ammonia, thus, hydration levels of a subject can be determined semi-quantitatively. In other embodiments, the level of the ammonia gas produced in 36 can be measured by a gas sensor as described above.

The apparatus 100/200/400 can also be used to detect other biomarker molecules through enzymatic action that generates target molecules which are present in the vapor phase at room temperature or have sufficient vapor pressure so that the target molecules can be readily detected in the vapor above an aqueous solution. The target molecules can be carbon monoxide, carbon dioxide, hydrocarbons, or other gases readily detectable in air. Several enzymatic reactions can generate hydrogen peroxide: (1) by adding the enzyme catalase, hydrogen peroxide can be converted to oxygen; (2) heme oxygenase produces carbon monoxide; and (3) isoprene may be detected from various metabolic reactions in other biological fluids and human breath.

Non-Limiting Example 1—Detection of Salivary Urea Nitrogen Using a Gas Sensor

Figure 5A:
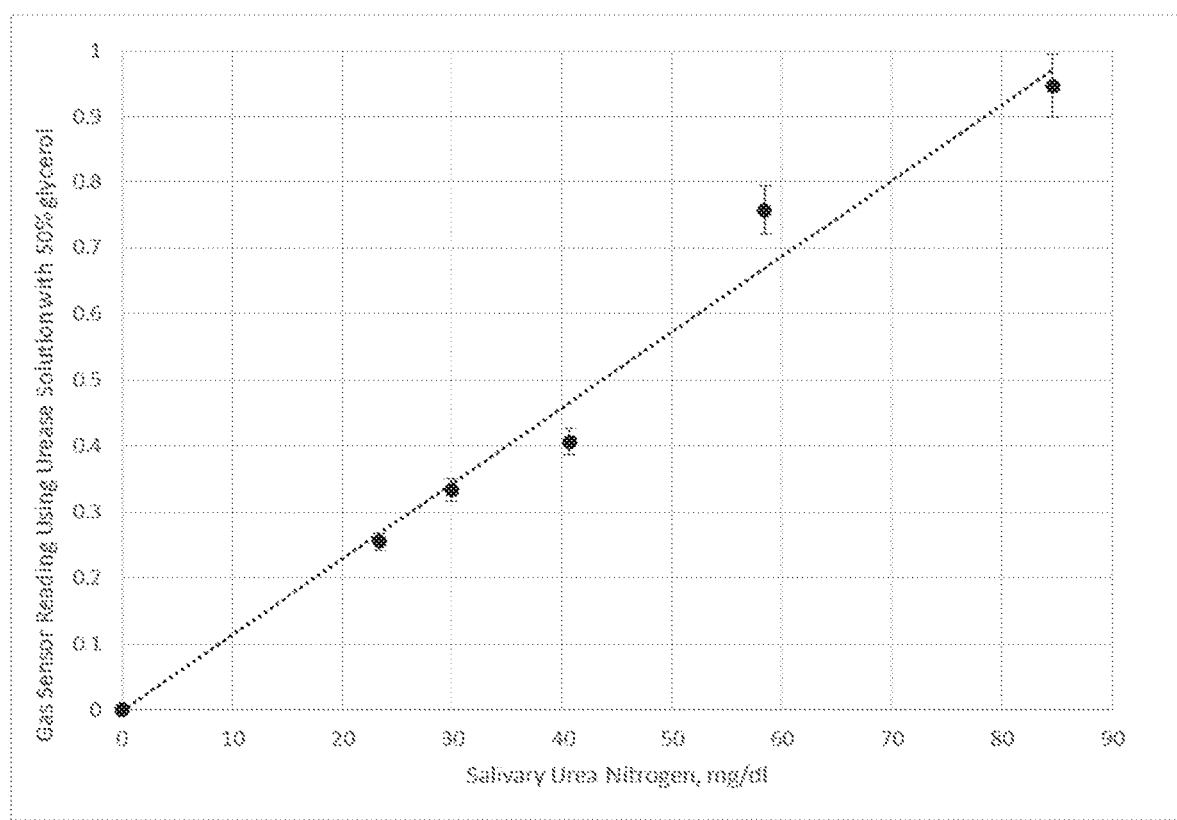
FIG. 5A shows linearity of the salivary urea nitrogen concentration generated from a gas sensor when using an enzyme solution with density and viscosity greater than saliva.
Figure 5B:
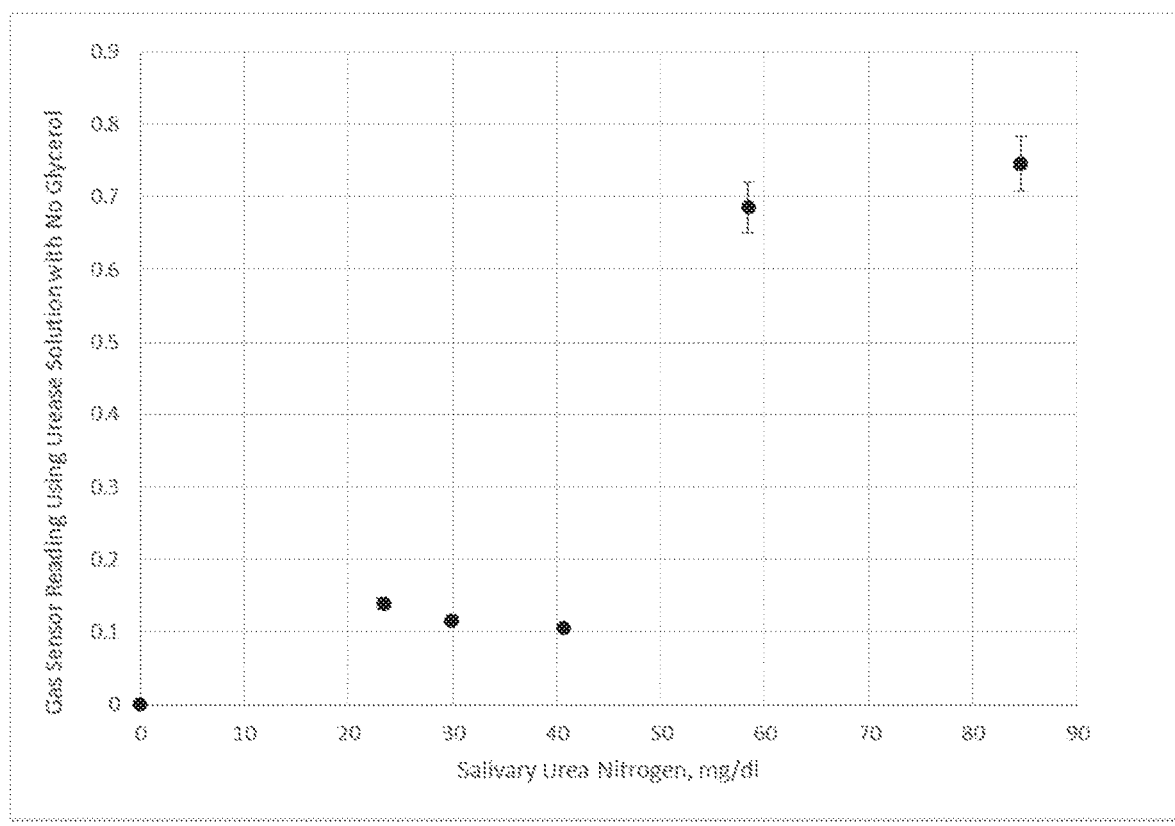
FIG. 5B illustrates that insufficient mixing of the testing sample and urease when using an enzyme solution that matches the density and viscosity of saliva produces non-linear

The porous gauze pad was loaded with 300 microliters of urease in 50% glycerol by volume with an enzyme activity of 6.4 units/ml. Buffer, saliva samples, and saliva samples containing added urea were analyzed twice by measuring the gas sensor voltage output over a total elapsed time of 15 minutes from when the sample was contacted with the porous gauze pad. Proper procedure for saliva collection consisted of drinking 5 ounces of water and refraining from food and drink for 30 minutes prior to sample collection. The collected saliva samples were not pretreated or diluted, and at least 300 microliters of sample is needed, although exact measurement is unnecessary due to the fixed liquid capacity of the gauze pad. All that was done once sufficient saliva is collected is to allow contact with the pad for 20 seconds in order for capillary action to be completed. The maximum average reading from 10 through 15 minutes after contact with the sample were referenced with buffer containing no urea and are graphed in FIG. 5A. Based on the technical literature, it is anticipated that normal salivary urea nitrogen level would mirror the levels in blood which is 7-20 mg/dl, correspond to a gas sensor reading of below 0.5, while a reading considered to be of concern would be above 50 mg/dl corresponding to a gas sensor reading above 1. This example teaches that saliva can be measured within the needed range to distinguish between normal salivary urea levels and up to very high levels of salivary urea nitrogen within 15 minutes.

Non-Limiting Example 2—Detection of Salivary Urea Nitrogen Using Color Indicators A very reliable, common, and simple way to measure urea in saliva is to use the enzyme urease to convert urea into ammonia. These two facts suggested to us that a key way of measuring urea in saliva is to rely on a very accurate method of detecting ammonia and employing urease in a simple and inexpensive way in a disposable kit format. Another important aspect of working with saliva is that it is pH buffered so that measuring ammonia by pH alone is prone to low sensitivity since ammonia at low levels will not raise the pH of a buffered solution and since the pH scale is logarithmic with respect to ammonia concentration. The current test apparatus can use the equilibrium ammonia concentration evolved at saliva pH and does not employ pH raising agents. In the current disclosure, ammonia gas is measured by adding a nanoporous water repellent membrane to cover the porous pad and placing color changing test pads or a gas sensor over the membrane.

A color changing test strip that is specific for ammonia regardless of pH and in order to keep the initial clinical testing simple is used. Particularly, Pad 1 as listed in Table 1 is the color indicator from Hach ammonia indicator test strip, and Pads 2 and 3 as listed in Table 1 are from Whatman, Panpeha Plus test strips that give color variations in the range 5.5-9.0 of pH. In the color indicator pads, ammonia permeating through the membrane is generating the color change, so the color does not reflect the pH of the liquid sample.

The porous gauze pad was loaded with 200 microliters of urease in 50% by volume of glycerol with an enzyme activity of 6.4 units/ml. Buffer, saliva samples, and saliva samples containing added urea were analyzed twice by measuring the gas sensor voltage output over a total elapsed time of 15 minutes from when the sample was contacted with the porous gauze pad. Proper procedure for saliva collection consisted of drinking 5 ounces of water and refraining from food and drink for 30 minutes prior to sample collection. The collected saliva samples were not pretreated or diluted, and at least 200 microliters of sample is needed, although exact measurement is unnecessary due to the fixed liquid capacity of the porous gauze pad. All that was done once sufficient saliva is collected. The saliva sample is allowed to contact the porous gauze pad for about 20 seconds in order for capillary action to be completed.

indicate that the saliva sample was properly detected. If a saliva sample does not register above the original color denoted as color scale level 1, then there was a problem with the sample or it is a negative control. However, Pad 1 is not very sensitive to changes in some of the lower parts of the salivary urea nitrogen scale and Pad 2 is best used for matching the color in the normal to borderline high level. In turn, Pad 3 becomes most useful in the high range. Above very high levels of salivary urea nitrogen, all of the color indicators achieve the maximum shade (level 7) within their respective scales. The technology determines the concentration of urea in saliva by generating a color change that can be observed visually and compared to a color chart. The concentration of urea in saliva correlates with hydration state of a person. The test is rapid, low cost, and does not require instrumentation or expert operation.

Non-Limiting Example 3

A very reliable, common, and simple way to measure urea in saliva is to use the enzyme Urease to convert urea into ammonia. These two facts suggested to us that a key way of measuring urea in saliva is to rely on a very accurate method of detecting ammonia and employing Urease in a simple and inexpensive way in a disposable kit format. Another important aspect of working with saliva is that it is pH buffered so that measuring ammonia by pH alone is prone to low sensitivity since ammonia at low levels will not raise the pH of a buffered solution and since the pH scale is logarithmic with respect to ammonia concentration.

Therefore, we chose a color changing test strip that is specific for ammonia regardless of pH and in order to keep the initial clinical testing simple, it was decided to use a commercial test strip that is calibrated for the low end of ammonia concentration (0-6 ppm). The test strip relies on measuring ammonia by raising the pH of the test solution to force ammonia to permeate a membrane by converting it from the ionic to its dissolved gas form. Due to the low range of the test strip, we employ a rapid means of removing high levels of ammonia in the saliva sample prior to the Urease reaction step. This step currently adds 5 minutes to the overall test, but very little cost due to the use of a small amount of ammonia cation exchange beads in a 3-D printed cartridge. An added advantage of scaling back the ammonia in saliva to low levels is that if a patient has high SUN for a period of time, there will be more ammonia left in the saliva sample and the combined test result will be an accurate, commensurately higher reading.

The information below describes our 10 Minute SUN kit results with healthy volunteers of ages 19-22 and 57. Also,

TABLE 1

Average values of Color Scale from lowest (1) to highest (7).

| Salivary Urea Nitrogen, mg/dl | Average Pad 1 Color Scale | Average Pad 2 Color Level | Average Pad 3 Color Level | Indicated Reading Using a Chart |
|---|---|---|---|---|
| 0 | 1 | 1 | 1 | No Urea/No sample |
| 23 | 2 | 2 | 2 | Normal |
| 30 | 3 | 5 | 5 | High |
| 41 | 3 | 5/6 | 5/6 | High |
| 58 | 5 | 6/7 | 6/7 | Mid-Range High |
| 85 | 7 | 7 | 7 | Highest Level |

As noted in Table 1, the color pads are used in combination within a chart developed based on observations of how the indicator paper responds to different levels of ammonia vapor above a pH 7 solution with a hydrophobic membrane barrier. The color variations as a group are useful for detecting a wider range since Pad 1 is mostly used to we have been employing a commercial skin impedance device as a reference when testing the "10 Minute SUN" disposable kit. This device (New Spa SK-02 Skin Analyzer) is one of many devices that provide dermatological information as the percent hydration of the skin, and it is not designed for medical purposes. Average readings of the face above 37% is considered normal, while readings from 32%-36% is considered dry and <31% is considered to be very dry skin.

10 Minute SUN Beta Test Kit Results

After calibrating the components of the test kit using laboratory instrumentation and simulated saliva solutions, we have completed two days of testing for all components of the kit. The data are summarized in the following table. Individual volunteers are referenced in the table using a 4-digit code. The results in Table 1 were useful to help illustrate that the beta 10 Minute SUN test kit can be performed easily outside of the laboratory (testing was done in an office), and that the information provided is within the expected range of values. These data are not referenced with specific SUN or BUN (blood urea nitrogen) values, due to the limited capabilities of our ASU laboratory for human testing. Qualitative information gathered during these two days of testing that is not reflected in the table is that the mucin in saliva made operating the steps easier by lubricating the 3-D printed devices used to remove excess ammonia from the acquired saliva sample as well as lubricating the 3-D printed slider with Urease enzyme immobilized on the slider pad.

support. The shelf life of the formulation has been tested in our refrigerator since July 2016, and we have thus far found that the enzyme appears to maintain its reactivity for 7 months. The entrapment method should extend the shelf life even more, based on the extensive literature of how immobilizing antibodies and enzymes increase shelf life of these proteins.

Non-Limiting Example 4

Using simulated saliva, experiments were conducted with 40 mg/dl and 10 mg/dl of Urea. The simulated saliva has buffering capacity to maintain the pH at 7.4, but with high ammonia production it is expected that buffering is not maintained. For 40 mg/dl Urea, complete conversion would result in approximately 227 ppm Ammonia, while for 10 mg/dl complete conversion would product 57 ppm Ammonia in solution.

A 12 mm×12 mm×3 mm thick porous gauze pad was soaked in 200 uL solution of 50 v. % glycerol/50 v. % water with urease and dried overnight in the refrigerator. The porous gauze pad was able to quickly wick up about 1 ml of simulated saliva. The porous gauze pad performed in the same manner when placed in a 3-D printed cartridge

TABLE 2

Summary of Beta 10 Minute SUN test kit results with skin impedance measurements for 3 volunteers.

| | | SKIN IMPEDANCE INFORMATION | | | | | SUN TEST RESULTS | | |
|---|---|---|---|---|---|---|---|---|---|
| ID | Date | Forehead | Face 1 | Face 2 | Neck | Wrist | Average | Test Strip Reading | Urea, mg/dl | Conclusion |
| 2108 | Feb. 21, 2017 | 36 | 33 | 33 | 33 | 34 | 34 | 3 | 10 | Normal |
| 2108 | Feb. 21, 2017 | 35 | 33 | 30 | 34 | 33 | 33 | 3 | 10 | Normal |
| 6113 | Feb. 22, 2017 | 37 | 32 | 34 | 36 | 34 | 35 | 6 | 30 | Normal |
| 6113 | Feb. 22, 2017 | 34 | 35 | 35 | 38 | 34 | 35 | 6 | 30 | Normal |
| 2210 | Feb. 23, 2017 | 30 | 34 | 34 | 35 | 32 | 33 | 6 | 30 | Normal |
| 2210 | Feb. 23, 2017 | 29 | 33 | 34 | 35 | 30 | 32 | 8 | 45 | Normal-High |
| 1234 | Feb. 21, 2017 | 39 | 39 | 37 | 42 | 38 | 39 | 6 | 30 | Normal |
| 1234 | Feb. 21, 2017 | 35 | 39 | 36 | 38 | 38 | 37 | 2 | 8 | Normal |
| 1234 | Feb. 22, 2017 | 40 | 39 | 37 | 44 | 40 | 40 | 7 | 40 | Normal |
| 1234 | Feb. 22, 2017 | 40 | 37 | 36 | 40 | 38 | 38 | 4 | 15 | Normal |
| 1234 | Feb. 23, 2017 | 38 | 8 | 36 | 38 | 34 | 31 | 7 | 40 | Normal |

Prior and post testing, Urease results and ammonia levels found in saliva were corroborated using a spectrometer to track the change in phenolphthalein with pH as ammonia is introduced or when Urease produces ammonia. A laboratory in the Biodesign Institute working to produce urease from waste seed has been working with our laboratory to compare the standard method of measuring Urease activity (e.g., Nessler Method) with our measurements, and there is a reasonably good agreement between the two. Our spectroscopic method does not produce any hazardous waste and is a relatively simple method that can be accomplished with a portable spectrometer as well, if additional field-lab testing is needed.

10 Minute SUN Beta Test Kit Details

The beta test kit uses plastic disposable components, a timer, and a color reference card. No power or measurement instrumentation is needed. The consumables of the test kit are provided in a sealed clear plastic container and should be stored in a refrigerator at approximately 4 oC, and the enzyme, beads, and test strip are expected to have a shelf life at 4 oC of up to one year. This is due to the way we stabilize the Urease through formulation and entrapment onto a solid assembled based on the line drawings. Measurements with several color indicator paper preparations with a gas permeable membrane showed that ammonia in the gas phase can be detected while the enzymatic reaction is taking place. Room temperature experiments indicate that after 5 minutes readings can be taken. The result of universal indicator paper color change indicated that 40 mg/dl Urea simulated saliva can be distinguished from 10 mg/dl simulated saliva. The calibration of the paper with ammonia standards in simulated saliva gives values of between 100-1,000 ppm ammonia for 40 mg/dl and 50 ppm ammonia for 10 mg/dl Urea. This is within the expected range.

Non-Limiting Example 5

An ammonia gas sensor (MQ 137) programmed to display voltage using an Arduino microcomputer was integrated into the SUN Device. Using 500 microliter pre imbibed Urease solution onto a gauze pad, 1 ml of simulated saliva at pH 7 containing either 10, 20, and 40 mg/dl of Urea respectively was applied to the pad and recording commenced immediately. The final design would use a "razor and blades" model whereby the gauze pad and saliva contacting portion would be detachable from the small sensor so that the electronics would be retained for more measurements while disposing of that portion of the device.

Figure 7:
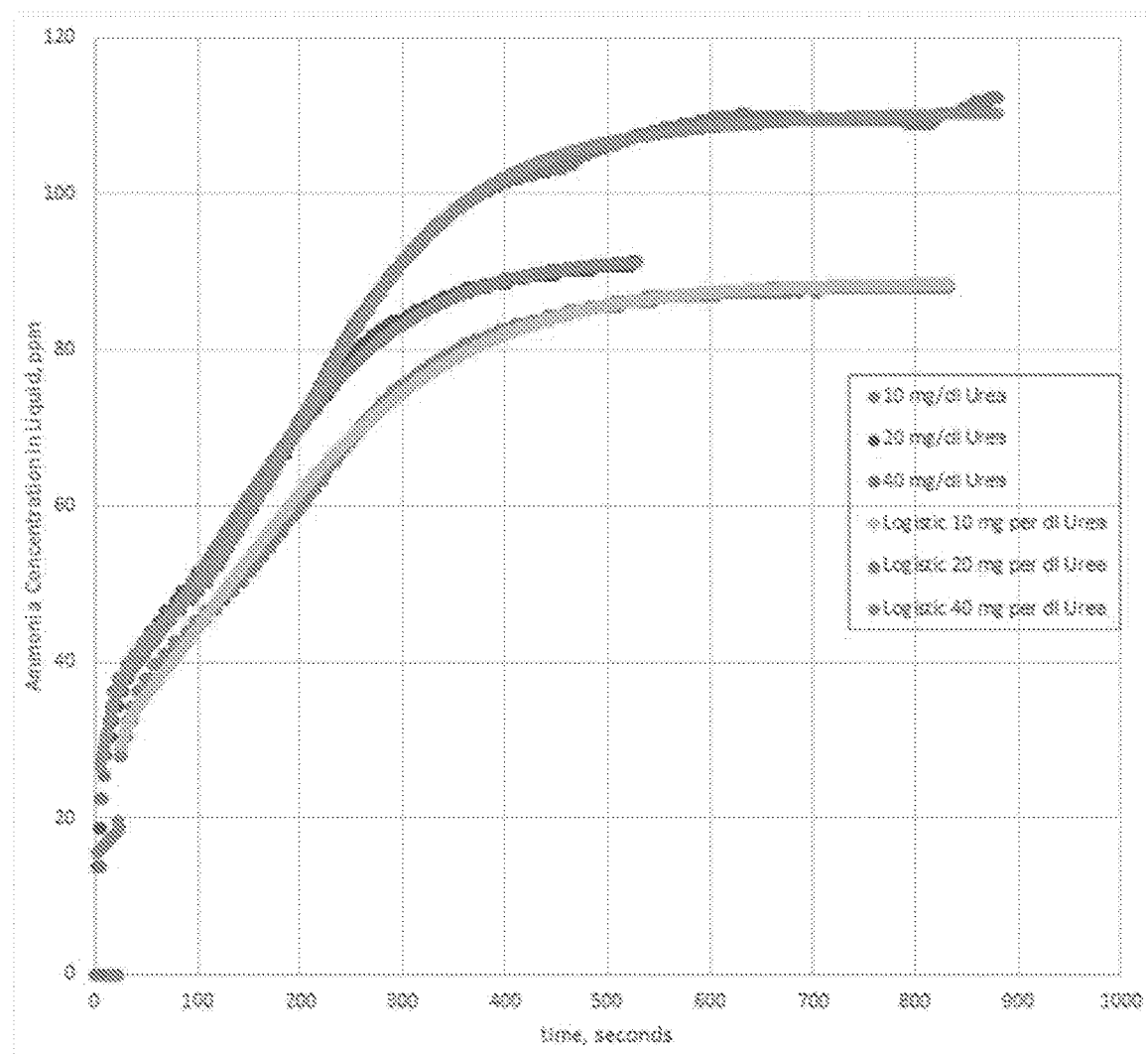
FIG. 7 shows a readout of different urea concentrations along a time scale.

The data and a mathematical curve fitting is given in FIG. 7. While the signal from the sensor is non-linear, the signal behavior is predictable due to the way that measurement is taken. First, at the very beginning of the reaction of Urease with urea the rate of signal generation is slow to register since ammonia generated is at low concentration and at pH 7, which means that most of the ammonia is not in the dissolved gas form. As the reaction continues and ammonia reaches threshold value, the rate is at its highest since the pH is at the optimum value for Urease activity of about pH=7-8. Once the amount of urea begins to be depleted and the concentration of ammonia increases enough to increase the pH of the solution, the rate of reaction slows but the signal continues to increase.

The mathematics of the signal generation can be modeled as a logistic curve series due to the different limitations in urea and enzyme activity as well as aqueous ammonia equilibria shift. In FIG. 7, it appears that reading the signal at 5 minutes (300 seconds) is a useful way to clearly distinguish between 10 mg/dl (75 ppm) and 20 mg/dl (84 ppm) of Urea, as well as a strong difference as compared to 40 mg/dl urea (92 ppm). The logistic series used to fit the data is of the form:

$$C(t) = \frac{K_1}{1+e^{-r_1(t-t_{1,0})}} + \frac{K_2}{1+e^{-r_2(t-t_{2,0})}} + \frac{K_3}{1+e^{-r_3(t-t_{3,0})}}$$

where the maximum concentration, rates, and initial times used for curve fitting are given in the table 2 below. The third term was only significant for curve fitting the highest urea concentration, which is understandable since the ammonia increase that shifts pH causes a more complex overall signal.

TABLE 3

| Urea Concentration, mg/dl | $K_1$ | $r_1$ | $t_{1,0}$ | $K_2$ | $r_2$ | $t_{2,0}$ | $K_3$ | $r_3$ | $t_{3,0}$ |
| --- | --- | --- | --- | --- | --- | --- | --- | --- | --- |
| 10 | 81 | .0087 | 119 | 7 | 0.21 | 23 | NA | NA | NA |
| 20 | 74 | .0835 | 120 | 18 | 0.0011 | 24 | NA | NA | NA |
| 40 | 62 | 0.013 | 200 | 24 | 0.0047 | 115 | 26 | .096 | 4 |

While the preferred embodiments of the present technology have been illustrated in detail, it should be apparent that modifications and adaptations to those embodiments may occur to one skilled in the art without departing from the scope of the present technology.

What is claimed is:

1. An apparatus comprising a porous pad for measuring a concentration of a target molecule from a biological sample, wherein:
   the porous pad is impregnated with a solution containing at least one agent configured to measure the concentration of the target molecule;
   the porous pad comprises an unfilled capillary matrix;
   the solution further comprises polyhydroxy organic compounds selected from the group consisting of glycerol, sucrose, polysorbate, ethylene glycol, propylene glycol, and a combination thereof; and
   the solution has a viscosity level higher than a viscosity of the biological sample to create viscous fingering instabilities.

2. The apparatus of claim 1, further comprising:
   a housing upon which the porous pad is disposed; and
   a membrane that covers the porous pad, wherein the membrane is hydrophobic and gas permeable.

3. The apparatus of claim 2, further comprising a target molecule level indicating strip disposed between the membrane and the porous pad.

4. The apparatus of claim 3, wherein the target molecule level indicating strip is configured as an indicator representing three different levels of a concentration of the target molecule with three different colors.

5. The apparatus of claim 2, further comprising a biological sample collecting device, wherein the device comprises:
   a funnel dimensioned to receive the biological sample;
   a container in fluid communication with the funnel and configured to store the biological sample; and
   a tray in fluid communication with the container and in fluid communication with the porous pad to have the porous pad absorb the biological sample.

6. The apparatus of claim 1, wherein the at least one agent is urease.

7. The apparatus of claim 1, wherein the porous pad is configured to absorb an amount of the biological sample that is sufficient for measuring the concentration of the target molecule.

8. The apparatus of claim 1, wherein the biological sample is blood, serum, plasma, urine, saliva, spinal fluid, sweat, tears, vaginal fluid, mucous, or semen.

9. The apparatus of claim 8, wherein the biological sample is saliva.

10. The apparatus of claim 9, wherein the target molecule is ammonia.

11. The apparatus of claim 1, further comprising a second porous pad impregnated with a second solution containing a second agent configured to react with creatinine to generate hydrogen peroxide.

12. A salivary urea nitrogen level testing kit comprising: a saliva collecting device, a porous pad, an ammonia level indicating strip, and a hydrophobic and gas permeable membrane disposed between the porous pad and the ammonia level indicating strip,
   wherein the saliva collecting device comprises a funnel configured to receive the saliva, a container in fluid communication with the funnel and configured to store the saliva, and a tray in fluid communication with the container and in fluid communication with the porous pad so that the porous pad is able to absorb the saliva.

13. The kit of claim 12, wherein the porous pad is impregnated with a solution containing urease and comprises unfilled capillary matrix.

14. The lit of claim 12, wherein the ammonia level indicating strip is configured as an indicator representing three different levels of ammonia concentration with three different colors.

15. The kit of claim 12, wherein the ammonia level indicating strip further comprises a liquid crystal display (LCD) readout panel, wherein the LCD readout panel is configured to display numerically a concentration of ammonia concentration.

16. A salivary urea nitrogen level testing kit comprising:
a saliva collecting device, a porous pad, a gas sensor, and a hydrophobic and gas permeable membrane disposed between the porous pad and the gas sensor,
wherein the saliva collecting device comprises a funnel configured to receive the saliva, a container in fluid communication with the funnel and configured to store the saliva, and a tray in fluid communication with the container and in fluid communication with the porous pad to have the porous pad absorb the saliva.

17. The kit of claim 16, wherein the porous pad is impregnated with a solution containing urease and comprises unfilled capillary matrix.

18. An apparatus comprising:
a porous pad comprising an unfilled capillary matrix, impregnated with a solution containing at least one agent, wherein the at least one agent is configured for measuring a concentration of a target molecule from a biological sample;
a housing upon which the porous pad is disposed;
a hydrophobic and gas permeable membrane that covers the porous pad;
and
a biological sample collecting device that includes:
a funnel dimensioned to receive the biological sample;
a container in fluid communication with the funnel and configured to store the biological sample; and
a tray in fluid communication with the container and in fluid communication with the porous pad.

19. The apparatus of claim 18, further comprising a target molecule level indicating strip disposed to sandwich the membrane between the target molecule level indicating strip and the porous pad.

20. The apparatus of claim 19, wherein the target molecule level indicating strip is configured as an indicator representing three different levels of the concentration of the target molecule with three different colors.

21. The apparatus of claim 18, wherein the at least one agent is urease.

22. The apparatus of claim 18, wherein the porous pad is configured to absorb an amount of the biological sample that is sufficient for measuring the concentration of the target molecule.

23. The apparatus of claim 18, wherein the solution further comprises polyhydroxy organic compounds selected from the group consisting of glycerol, sucrose, polysorbate, ethylene glycol, propylene glycol, and a combination thereof; and the solution has a viscosity level higher than a viscosity of the biological sample to create viscous fingering instabilities.

24. The apparatus of claim 18, wherein the biological sample is blood, serum, plasma, urine, saliva, spinal fluid, sweat, tears, vaginal fluid, mucous, or semen.

25. The apparatus of claim 24, wherein the biological sample is saliva.

26. The apparatus of claim 25, wherein the target molecule is ammonia.

27. The apparatus of claim 18, further comprising a second porous pad impregnated with a second solution containing a second agent configured to react with creatinine to generate hydrogen peroxide.

* * * * *